US007618522B2

(12) United States Patent  
Davies

(10) Patent No.: US 7,618,522 B2
(45) Date of Patent: *Nov. 17, 2009

(54) METHOD OF REDUCING INTERFERENCES IN AN ELECTROCHEMICAL SENSOR USING TWO DIFFERENT APPLIED POTENTIALS

(75) Inventor: Oliver William Hardwicke Davies, Croy (GB)

(73) Assignee: Lifescan Scotland Limited, Inverness-Shire (GB)

( * ) Notice: Subject to any disclaimer, the term of this patent is extended or adjusted under 35 U.S.C. 154(b) by 875 days.

This patent is subject to a terminal disclaimer.

(21) Appl. No.: 10/977,154

(22) Filed: Oct. 29, 2004

(65) Prior Publication Data

US 2005/0183965 A1   Aug. 25, 2005

Related U.S. Application Data

(60) Provisional application No. 60/516,252, filed on Oct. 31, 2003, provisional application No. 60/558,728, filed on Mar. 31, 2004, provisional application No. 60/558,427, filed on Mar. 31, 2004.

(51) Int. Cl.
*C12Q 1/54* (2006.01)
*C12Q 1/26* (2006.01)
*C12Q 1/00* (2006.01)

(52) U.S. Cl. ............... 204/403.14; 205/775; 205/777.5; 205/792

(58) Field of Classification Search ............ 204/403.14; 205/775, 777.5, 792
See application file for complete search history.

(56) References Cited

U.S. PATENT DOCUMENTS 4,233,031 A * 11/1980 Matson et al. ........... 205/789.5

| | | | |
|---|---|---|---|
| 4,431,004 A | 2/1984 | Bessman et al. | |
| 4,655,880 A | 4/1987 | Liu et al. | |
| 5,298,146 A * | 3/1994 | Braden et al. | 204/406 |
| 5,582,697 A | 12/1996 | Ikeda et al. | |
| 5,628,890 A | 5/1997 | Carter et al. | |
| 5,650,062 A | 7/1997 | Ikeda et al. | |

(Continued)

FOREIGN PATENT DOCUMENTS

| WO | WO 89/02593 A | 3/1989 |
|---|---|---|
| WO | 99/013099 A1 | 3/1999 |
| WO | WO 99/13099 A1 | 3/1999 |
| WO | WO 00/79258 A1 | 12/2000 |
| WO | WO 01/67099 | 9/2001 |
| WO | WO 01/73124 | 10/2001 |
| WO | WO 02/49507 | 6/2002 |
| WO | WO 2004/029605 A | 4/2004 |
| WO | WO 2004/039600 A2 | 5/2004 |
| WO | 2005/045412 A1 | 5/2005 |

OTHER PUBLICATIONS

International Search Report, European Patent Office, Rijswijk, NL, Feb. 7, 2005; International Application for PCT/GB2004/004588.

(Continued)

*Primary Examiner*—Nam X Nguyen
*Assistant Examiner*—J. Christopher Ball
(74) *Attorney, Agent, or Firm*—Khoi Ta

(57) ABSTRACT

The present invention is directed to a method of reducing the effects of interfering compounds in the measurement of analytes and more particularly to a method of reducing the effects of interfering compounds in a system wherein the test strip utilizes two or more working electrodes. In one embodiment of the present invention, a first potential is applied to a first working electrode and a second potential, having the same polarity but a greater magnitude than the first potential, is applied to a second working electrode.

6 Claims, 3 Drawing Sheets

U.S. PATENT DOCUMENTS

| | | |
|---|---|---|
| 5,653,918 A | 8/1997 | Towlson |
| 5,708,247 A | 1/1998 | McAleer et al. |
| 5,830,343 A | 11/1998 | Hintsche et al. |
| 5,985,116 A | 11/1999 | Ikeda et al. |
| 6,046,051 A | 4/2000 | Jina et al. |
| 6,212,417 B1 | 4/2001 | Ikeda et al. |
| 6,258,229 B1 | 7/2001 | Winarta et al. |
| 6,287,451 B1 * | 9/2001 | Winarta et al. ........... 205/777.5 |
| 6,540,891 B1 | 4/2003 | Stewart et al. |
| 6,730,200 B1 | 5/2004 | Stewart et al. |
| RE38,681 E | 1/2005 | Kurnik et al. |
| 7,132,041 B2 | 11/2006 | Deng et al. |
| 2002/0020632 A1 * | 2/2002 | Douglas et al. .......... 205/777.5 |
| 2002/0092612 A1 | 7/2002 | Davies et al. |
| 2002/0157947 A1 | 10/2002 | Rappin et al. |
| 2002/0168290 A1 | 11/2002 | Yuzhakov et al. |
| 2003/0143113 A2 | 7/2003 | Yuzhakov |
| 2004/0120848 A1 | 6/2004 | Teodorczyk |
| 2004/0149578 A1 | 8/2004 | Huang |
| 2005/0114062 A1 | 5/2005 | Davies et al. |
| 2005/0139469 A1 | 6/2005 | Davies et al. |
| 2005/0139489 A1 | 6/2005 | Davies et al. |

OTHER PUBLICATIONS

International Search Report, European Patent Office, Rijswijk, NL, Feb. 2, 2005; International Application for PCT/GB2004/004598.

International Search Report, European Patent Office, Rijswijk, NL, Jan. 31, 2005; International Application for PCT/GB2004/004592.

International Search Report, European Patent Office, Rijswijk, NL, Feb. 4, 2005; International Application for PCT/GB2004/004594.

Harrington M.S. et al; "Multiple Electrode Potentiostat" Review of Scientific Instruments, American Institute of Physics. New York, US, vol. 60, No. 10, Oct. 1, 1989, pp. 3323-3328, XP000071728 ISSN: 0034-6748 abstract; figs. 2,6.

International Search Report, European Patent Office, Rijswijk, NL, Feb. 1, 2005; International application for PCT/GB2004/004574.

Matsue, T., et al. "Multichannel electrochemical detection system for flow analysis", Analytical Chemistry, vol. 62, No. 4, Feb. 15, 1990, p. 407-409.

* cited by examiner

METHOD OF REDUCING INTERFERENCES IN AN ELECTROCHEMICAL SENSOR USING TWO DIFFERENT APPLIED POTENTIALS

RELATED APPLICATIONS

The present invention is related to the following co-pending U.S. applications: U.S. patent application Ser. No. 10/977,155, filed on Oct. 29, 2004; U.S. patent application Ser. No. 10/976,489, filed on Oct. 29, 2004; U.S. patent application Ser. No. 10/977,292, filed on Oct. 29, 2004; U.S. patent application Ser. No. 10/977,292, filed on Oct. 29, 2004; and U.S. patent application Ser. No. 10/977,086, filed on Oct. 29, 2004.

BACKGROUND OF INVENTION

PRIORITY

This application claims priority from Provisional Application No. 60/516,252 filed Oct. 31, 2003, Provisional Application No. 60/558,728 filed Mar. 31, 2004, and Provisional Application No. 60/558,427 filed Mar. 31, 2004, which are incorporated herein by reference and to which we claim priority.

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose is based upon the specific oxidation of glucose by the flavo-enzyme glucose oxidase. During this reaction, the enzyme becomes reduced. The enzyme is re-oxidised by reaction with the mediator ferricyanide, which is itself reduced during the course or the reaction. These reactions are summarized below.

$$D\text{-Glucose} + GOx_{(ox)} \rightarrow \text{Gluconic acid} + GOx_{(RED)}$$

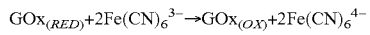

$$GOx_{(RED)} + 2Fe(CN)_6^{3-} \rightarrow GOx_{(OX)} + 2Fe(CN)_6^{4-}$$

When the reaction set forth above is conducted with an applied potential between two electrodes, an electrical current may be created by the electrochemical re-oxidation of the reduced mediator ion (ferrocyanide) at the electrode surface. Thus, since, in an ideal environment, the amount of ferrocyanide created during the chemical reaction described above is directly proportional to the amount of glucose in the sample positioned between the electrodes, the current generated would be proportional to the glucose content of the sample. A redox mediator, such as ferricyanide is a compound that exchanges electrons between a redox enzyme such as glucose oxidase and an electrode. As the concentration of glucose in the sample increases, the amount of reduced mediator formed also increases, hence, there is a direct relationship between current resulting from the re-oxidation of reduced mediator and glucose concentration. In particular, the transfer of electrons across the electrical interface results in a flow of current (2 moles of electrons for every mole of glucose that is oxidized). The current resulting from the introduction of glucose may, therefore, be referred to as the glucose current.

Because it can be very important to know the concentration of glucose in blood, particularly in people with Diabetes, meters have been developed using the principals set forth above to enable the average person to sample and test their blood to determine the glucose concentration at any given time. The Glucose Current generated is monitored by the meter and converted into a reading of glucose concentration using a preset algorithm that relates current to glucose concentration via a simple mathematical formula. In general, the meters work in conjunction with a disposable strip that includes a sample chamber and at least two electrodes disposed within the sample chamber in addition to the enzyme (e.g. glucose oxidase) and mediator (e.g. ferricyanide). In use, the user pricks their finger or other convenient site to induce bleeding and introduces a blood sample to the sample chamber, thus starting the chemical reaction set forth above.

In electrochemical terms, the function of the meter is two fold. Firstly, it provides a polarizing voltage (approximately 0.4 V in the case of OneTouch® Ultra®) that polarizes the electrical interface and allows current flow at the carbon working electrode surface. Secondly, it measures the current that flows in the external circuit between the anode (working electrode) and the cathode (reference electrode). The meter may, therefore be considered to be a simple electrochemical system that operates in two-electrode mode although, in practice, third and, even fourth electrodes may be used to facilitate the measurement of glucose and/or perform other functions in the meter.

In most situations, the equation set forth above is considered to be a sufficient approximation of the chemical reaction taking place on the test strip and the meter reading a sufficiently accurate representation of the glucose content of the blood sample. However, under certain circumstances and for certain purposes, it may be advantageous to improve the accuracy of the measurement. For example, where a portion of the current measured at the electrode results from the presence of other chemicals or compounds in the sample. Where such additional chemicals or compounds are present, they may be referred to as interfering compounds and the resulting additional current may be referred to as Interfering Currents.

Examples of potentially interfering chemicals (i.e. compounds found in physiological fluids such as blood that may generate Interfering Currents in the presence of an electrical field) include ascorbate, urate and acetaminophen (Tylenol™ or Paracetamol). One mechanism for generating Interfering Currents in an electrochemical meter for measuring the concentration of an analyte in a physiological fluid (e.g. a glucose meter) involves the oxidation of one or more interfering compounds by reduction of the enzyme (e.g. glucose oxidase). A further mechanism for generating Interfering Currents in such a meter involves the oxidation of one or more interfering compounds by reduction of the mediator (e.g. ferricyanide). A further mechanism for generating Interfering Currents in such a meter involves the oxidation of one or more interfering compounds at the working electrode. Thus, the total current measured at the working electrode is the superposition of the current generated by oxidation of the analyte and the current generated by oxidation of interfering compounds. Oxidation of interfering compounds may be a result of interaction with the enzyme, the mediator or may occur directly at the working electrode.

In general, potentially interfering compounds can be oxidized at the electrode surface and/or by a redox mediator. This oxidation of the interfering compound in a glucose measurement system causes the measured oxidation current to be dependent on both the glucose and the interfering compound. Therefore, if the concentration of interfering compound oxidizes as efficiently as glucose and/or the interfering compound concentration is significantly high relative to the glucose concentration, it may impact the measured glucose concentration.

The co-oxidization of analyte (e.g. glucose) with interfering compounds is especially problematic when the standard potential (i.e. the potential at which a compound is oxidized)

of the interfering compound is similar in magnitude to the standard potential of the redox mediator, resulting in a significant portion of the Interference Current being generated by oxidation of the interfering compounds at the working electrode. Electrical current resulting from the oxidation of interfering compounds at the working electrode may be referred to as direct interference current. It would, therefore, be advantageous to reduce or minimize the effect of the direct interference current on the measurement of analyte concentration. Previous methods of reducing or eliminating direct interference current include designing test strips that prevent the interfering compounds from reaching the working electrode, thus reducing or eliminating the direct interference current attributable to the excluded compounds.

One strategy for reducing the effects of interfering compounds that generate Direct interference current is to place a negatively charged membrane on top of the working electrode. As one example, a sulfonated fluoropolymer such as NAFION™ may be placed over the working electrode to repel all negatively charged chemicals. In general, many interfering compounds, including ascorbate and urate, have a negative charge, and thus, are excluded from being oxidized at the working electrode when the surface of the working electrode is covered by a negatively charged membrane. However, because some interfering compounds, such as acetaminophen, are not negatively charged, and thus, can pass through the negatively charged membrane, the use of a negatively charged membrane will not eliminate the Direct interference current. Another disadvantage of covering the working electrode with a negatively charged membrane is that commonly used redox mediators, such as ferricyanide, are negatively charged and cannot pass through the membrane to exchange electrons with the electrode. A further disadvantage of using a negatively charged membrane over the working electrode is the potential to slow the diffusion of the reduced mediator to the working electrode, thus increasing the test time. A further disadvantage of using a negatively charged membrane over the working electrode is the increased complexity and expense of manufacturing the test strips with a negatively charged membrane.

Another strategy that can be used to decrease the effects of Direct Interfering Currents is to position a size selective membrane on top of the working electrode. As one example, a 100 Dalton size exclusion membrane such as cellulose acetate may be placed over the working electrode to exclude compounds having a molecular weight greater than 100 Daltons. In this embodiment, the redox enzyme such as glucose oxidase is positioned over the size exclusion membrane. Glucose oxidase generates hydrogen peroxide, in the presence of glucose and oxygen, in an amount proportional to the glucose concentration. It should be noted that glucose and most redox mediators have a molecular weight greater than 100 Daltons, and thus, cannot pass through the size selective membrane. Hydrogen peroxide, however, has a molecular weight of 34 Daltons, and thus, can pass through the size selective membrane. In general, most interfering compounds have a molecular weight greater than 100 Daltons, and thus, are excluded from being oxidized at the electrode surface. Since some interfering compounds have smaller molecular weights, and thus, can pass through the size selective membrane, the use of a size selective membrane will not eliminate the Direct interference current. A further disadvantage of using a size selective membrane over the working electrode is the increased complexity and expense of manufacturing the test strips with a size selective membrane.

Another strategy that can be used to decrease the effects of Direct interference current is to use a redox mediator with a low redox potential, for example, a redox potential of between about −300 mV to +100 mV (vs a saturated calomel electrode). This allows the applied potential to the working electrode to be relatively low which, in turn, decreases the rate at which interfering compounds are oxidized by the working electrode. Examples of redox mediators having a relatively low redox potential include osmium bipyridyl complexes, ferrocene derivatives, and quinone derivatives. However, redox mediators having a relatively low potential are often difficult to synthesize, relatively unstable and relatively insoluble.

Another strategy that can be used to decrease the effects of interfering compounds is to use a dummy electrode in conjunction with the working electrode. The current measured at the dummy electrode may then be subtracted from the current measured at the working electrode in order to compensate for the effect of the interfering compounds. If the dummy electrode is bare (i.e. not covered by an enzyme or mediator), then the current measured at the dummy electrode will be proportional to the Direct interference current and subtracting the current measured at the dummy electrode from the current measured at the working electrode will reduce or eliminate the effect of the direct oxidation of interfering compounds at the working electrode. If the dummy electrode is coated with a redox mediator then the current measured at the dummy electrode will be a combination of Direct interference current and interference current resulting from reduction of the redox mediator by an interfering compound. Thus, subtracting the current measured at the dummy electrode coated with a redox mediator from the current measured at the working electrode will reduce or eliminate the effect of the direct oxidation of interfering compounds and the effect of interference resulting from reduction of the redox mediator by an interfering compound at the working electrode. In some instances the dummy electrode may also be coated with an inert protein or deactivated redox enzyme in order to simulate the effect of the redox mediator and enzyme on diffusion. Because it is preferable that test strips have a small sample chamber so that people with diabetes do not have to express a large blood sample, it may not be advantageous to include an extra electrode which incrementally increases the sample chamber volume where the extra electrode is not used to measure the analyte (e.g. glucose). Further, it may be difficult to directly correlate the current measured at the dummy electrode to interference currents at the working electrode. Finally, since the dummy electrode may be coated with a material or materials (e.g. redox mediator) which differ from the materials used to cover the working electrode (e.g. redox mediator and enzyme), test strips which use dummy electrodes as a method of reducing or eliminating the effect of interfering compounds in a multiple working electrode system may increase the cost and complexity of manufacturing the test strip.

Certain test strip designs which utilize multiple working electrodes to measure analyte, such as the system used in the OneTouch® Ultra® glucose measurement system are advantageous because the use of two working electrodes. In such systems, it would, therefore, be advantageous to develop a method of reducing or eliminating the effect of interfering compounds. More particularly, it would be advantageous to develop a method of reducing or eliminating the effect of interfering compounds without utilizing a dummy electrode, an intermediate membrane or a redox mediator with a low redox potential.

SUMMARY OF INVENTION

The present invention is directed to a method of reducing the effects of interfering compounds in the measurement of analytes and more particularly to a method of reducing the effects of interfering compounds in a system wherein the test strip utilizes two or more working electrodes. In one embodiment of the present invention, a first potential is applied to a first working electrode and a second potential, having the same polarity but a greater magnitude than the first potential, is applied to a second working electrode. The magnitude of the second potential may also be less than the first potential for an embodiment where a reduction current is used to measure the analyte concentration. In one embodiment, the first working electrode and second working electrode may be covered with an enzyme reagent and redox mediator that are analyte specific. The first potential applied to the first working electrode is selected such that it is sufficient to oxidize reduced redox mediator in a diffusion limited manner while the second potential is selected to have a magnitude (i.e. absolute value) greater than the magnitude of the first potential, resulting in a more efficient oxidation of at the second working electrode. In this embodiment of the invention, the current measured at the first working electrode includes an analyte current and interfering compound current while the current measured at the second working electrode includes an analyte overpotential current and an interfering compound overpotential current. It should be noted that the analyte current and the analyte overpotential current both refer to a current that corresponds to the analyte concentration and that the current is a result of a reduced mediator oxidation. In an embodiment of this invention, the relationship between the currents at the first working electrode and second working electrode may be defined by the following equation, $$A_1 = \frac{W_2 - YW_1}{X - Y}$$

where $A_1$ is the analyte current at the first working electrode, $W_1$ is the current measured at the first working electrode, $W_2$ is the current measured at the second working electrode, $X$ is an analyte dependent voltage effect factor and $Y$ is an interfering compound dependent voltage effect factor. Using the equation set forth above, in a method according to the present invention, it is possible to reduce the effect of oxidation currents resulting from the presence of interfering compounds and calculate a corrected current value that is more representative of the concentration of analyte in the sample being measured.

In one embodiment of the present invention, the concentration of glucose in a sample placed on a test strip can be calculated by placing the sample on a test strip having a first working electrode and second working electrode and a reference electrode, at least the first working electrode and second working electrodes being coated with chemical compounds (e.g. an enzyme and a redox mediator) adapted to facilitate the oxidation of glucose and the transfer of electrons from the oxidized glucose to the first working electrode and the second working electrode when a potential is applied between the first working electrode and the reference electrode, and the second working electrode and the reference electrode. In accordance with the present invention, a first potential is applied between the first working electrode and the reference electrode, the first potential being selected to have a magnitude sufficient to ensure that the magnitude of the current generated by oxidation of the glucose in the sample is limited only by factors other than applied voltage (e.g. diffusion). In accordance with the present invention, a second potential is applied between the second working electrode and the reference electrode, the second potential being greater in magnitude than the first potential and, in one embodiment of the present invention, the second potential being selected to increase the oxidation of interfering compounds at the second working electrode. In a further embodiment of the present invention, the following equation may be used to reduce the effect of oxidation current resulting from the presence of interfering compounds on the current used to calculate the concentration of glucose in the sample. In particular, the glucose concentration may be derived using a calculated current $A_{1G}$ where:

$$A_{1G} = \frac{W_2 - YW_1}{X_G - Y}$$

where $A_{1G}$ is a glucose current, $W_1$ is the current measured at the first working electrode, $W_2$ is the current measured at the second working electrode, $X_G$ is a glucose dependent voltage effect factor and $Y$ is an interfering compound dependent voltage effect factor.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
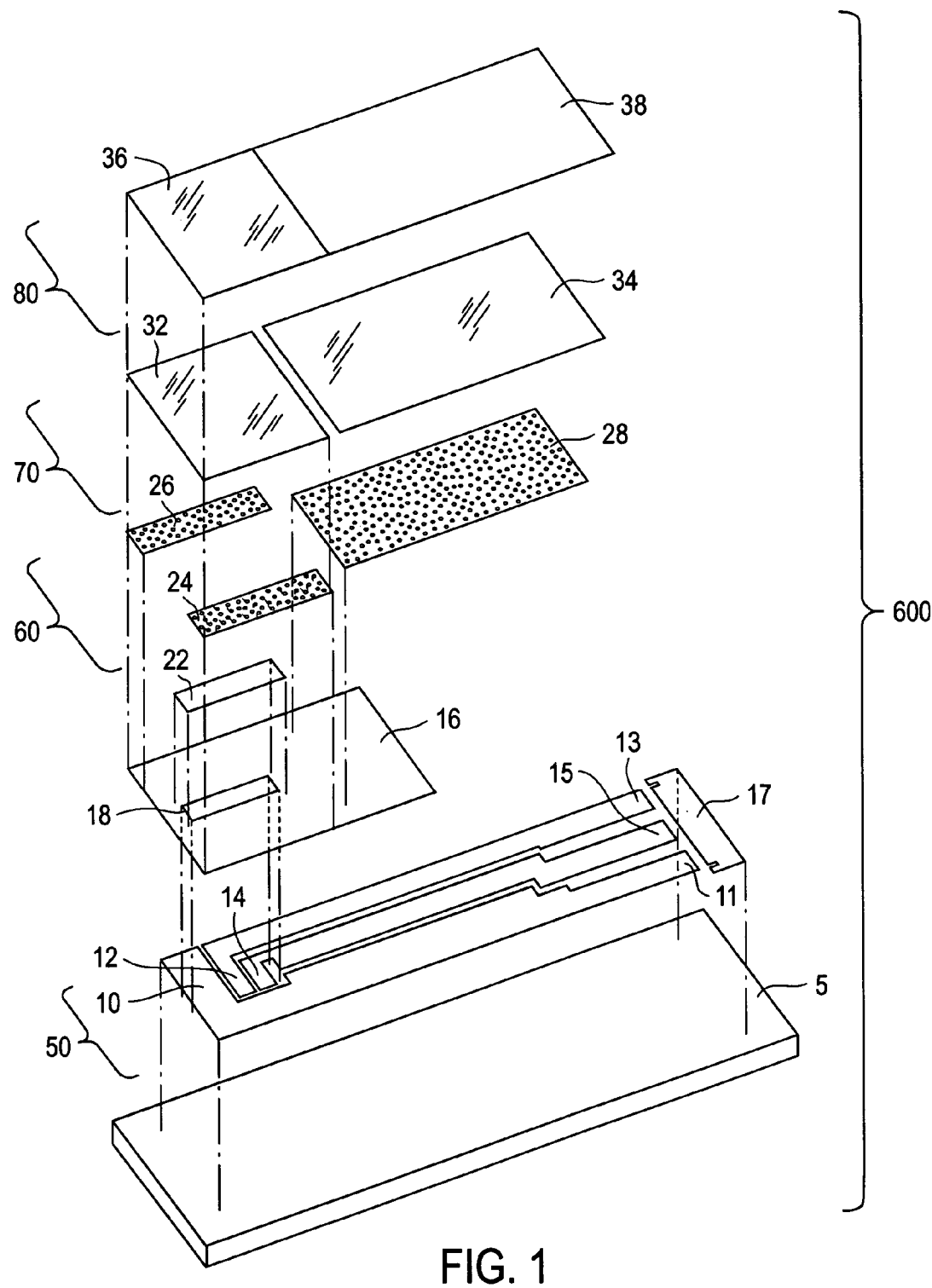
FIG. 1 is an exploded perspective view of a test strip embodiment for use in the present invention.

While the present invention is particularly adapted to the measurement of glucose concentration in blood, it will be apparent to those of skill in the art that the method described herein may be adapted to improve the selectivity of other systems used for the electrochemical measurement of analytes in physiological fluids. Examples of systems that may be adapted to improve selectivity using the method according to the present invention include electrochemical sensors used to measure the concentration of lactate, lactate, alcohol, cholesterol, amino acids, choline, and fructosamine in physiological fluids. Examples of physiological fluids that may contain such analytes include blood, plasma, serum, urine, and interstitial fluid. It will further be understood that, while the method of the present invention is described in an electrochemical system where the measured current is produced by oxidation, the invention would be equally applicable to a system wherein the measured current is produced by reduction.

The present invention is directed to a method for improving the selectivity of an electrochemical measuring system that is particularly adapted for use in a blood glucose measurement system. More particularly, the present invention is directed to a method for improving the selectivity of a blood glucose measurement system by partially or wholly correcting for the effect of the direct interference current. Selectivity in such systems being a measure of the ability of the system to accurately measure the glucose concentration in a sample of physiological fluid which includes one or more compounds which create an interfering current. Improvement of selectivity thus reduces the current generated at the working electrode by the presence of interfering compounds (i.e. compounds other than glucose which oxidize to generate interfering current) and makes the measured current more representative of the glucose concentration. In particular, the measured current may be a function of the oxidation of interfering compounds commonly found in physiological fluids such as, for example, acetaminophen (Tylenol™ or Paracetamol), ascorbic acid, bilirubin, dopamine, gentisic acid, glutathione, levodopa, methyldopa, tolazimide, tolbutamide and uric acid. Such interfering compounds may be oxidized by, for example, reacting chemically with the redox mediator or by oxidizing at the electrode surface.

In a perfectly selective system, there would be no oxidation current generated by any interfering compound and the entire oxidation current would be generated by oxidation of glucose. However, if oxidation of interfering compounds and the resulting oxidation current cannot be avoided the present invention describes a method of removing some or all of the effect of interfering compounds by quantifying the proportion of the overall oxidation current generated by the interfering compounds and subtracting that quantity from the overall oxidation current. In particular, in a method according to the present invention, using a test strip that includes first working electrode and second working electrode, two different potentials are applied and the oxidation current generated at each of the working electrodes is measure used to estimate the respective oxidation current proportions for both the glucose and interfering compounds.

In one embodiment of a method according to the present invention, a test strip is used which includes a sample chamber containing a first working electrode, a second working electrode, and a reference electrode. The first working electrode, the second working electrode and the reference electrodes are covered by glucose oxidase (the enzyme) and a Ferricyanide (the redox mediator). When a sample of blood (the physiological fluid) is placed in the sample chamber, the glucose oxidase is reduced by glucose in the blood sample generating gluconic acid. The gluconic acid is then oxidized by reduction of the Ferricyanide to Ferrocyanide, yielding a reduced redox mediator with a concentration proportional to the glucose concentration. An example of a test strip that may be suitable for use in a method according to the present invention is the OneTouch® Ultra® test strip sold by Life Scan, Inc. of Milpitas, Calif. Other suitable strips are described in international publication WO 01/67099A1 and WO 01/73124A2.

In one embodiment of a method according to the present invention a first potential is applied to a first working electrode and a second potential is applied to the second working electrode. In this embodiment, the first potential is selected to be in a range in which the glucose current response is relatively insensitive to the applied potential and thus the magnitude of the glucose current at the first working electrode is limited by the amount of reduced redox mediator diffusing to the first working electrode. It should be noted that glucose is not directly oxidized at a working electrode, but instead is indirectly oxidized through using a redox enzyme and a redox mediator. In the description of the present invention, the glucose current refers to an oxidation of reduced redox mediator that correlates to the gluocose concentration. In an embodiment of the present invention where ferri/ferrocyanide is the redox mediator and carbon is the working electrode, the first potential may range from about 0 millivolts to about 500 millivolts, and more preferably from about 385 millivolts to about 415 millivolts, and yet even more preferably may range from about 395 to 405 mV. A second potential is applied to a second working electrode such that the second potential is greater than the first potential. Where the applied potential is greater than the potential needed to oxidize the glucose. In an embodiment of the present invention where ferri/ferrocyanide is the redox mediator and carbon is the working electrode, the second potential may range from about 50 millivolts to about 1000 millivolts, and more preferably from about 420 millivolts to about 1000 millivolts.

Because the glucose current does not increase or increases only minimally with increasing potential, the glucose current at the second working electrode should be substantially equal to the glucose current at the first working electrode, even though the potential at the second working electrode is greater than the potential at the first electrode. Thus, any additional current measured at the second working electrode may be attributed to the oxidation of interfering compounds. In other words, the higher potential at the second working electrode should'cause a glucose overpotenital current to be measured at the second working electrode which is equal or substantially equal in magnitude to the glucose current at the first working electrode because the first potential and second potential are in a limiting glucose current range which is insensitive to changes in applied potential. However, in practice, other parameters may have an impact on the measured current, for example, where a higher potential is applied to the second working electrode, there is often a slight increase in the overall current at the second working electrode as a result of an IR drop or capacitive effects. When an IR drop (i.e. uncompensated resistance) is present in the system, a higher applied potential causes an increase in the measured current magnitude. Examples of IR drops may be the nominal resistance of the first working electrode, second working electrode, the reference electrode, the physiological fluid between the working electrode and the reference electrode. In addition, the application of a higher potential results in the formation of a larger ionic double layer which forms at the electrode/liquid interface, increasing the ionic capacitance and the resulting current at either the firstworking electrode or second working electrode.

In order to determine the actual relationship between the glucose current measured at the first working electrode and the second working electrode, it is necessary to develop a suitable equation. It should be noted that the glucose current at the second working electrode may also be referred to as a glucose overpotential current. A directly proportional relationship between the glucose current and the glucose overpotential current may be described by the following equation.

$$X_G \times A_{1G} = A_{2G} \quad (\text{eq 1})$$

where $X_G$ is a glucose dependent voltage effect factor, $A_{1G}$ is the glucose current at the first working electrode and A2G is the glucose current at the second working electrode.

In an embodiment of the present invention, where ferri/ferrocyanide is the redox mediator and carbon is the working electrode, the voltage effect factor $X_G$ for glucose may be expected to be between about 0.95 any about 1.1. In this embodiment of the invention, higher potentials do not have a significant impact on the glucose oxidation current because the redox mediator (ferrocyanide) has fast electron transfer kinetics and reversible electron transfer characteristics with the working electrode. Because the, glucose current does not increase with increasing potential after a certain point, the glucose current may be said to be saturated or in a diffusion limited regime.

In the embodiment of the present invention described above, glucose is indirectly measured by oxidizing ferrocyanide at the working electrode and where the ferrocyanide concentration is directly proportional to the glucose concentration. The standard potential (E°) value for a particular electrochemical compound is a measure of that compound's ability to exchange electrons with other chemical compounds. In the method according to the present invention, the potential at the first working electrode is selected to be greater than the standard potential (E°) of the redox mediator. Because the first potential is selected such that it is sufficiently greater than the E° value of the redox couple, the oxidation rate does not increase substantially as the applied potential increases. Thus, applying a greater potential at the second working electrode will not increase the oxidation at the second working electrode and any increased current measured at the higher potential electrode must be due to other factors, such as, for example, oxidation of interfering compounds.

Figure 3:
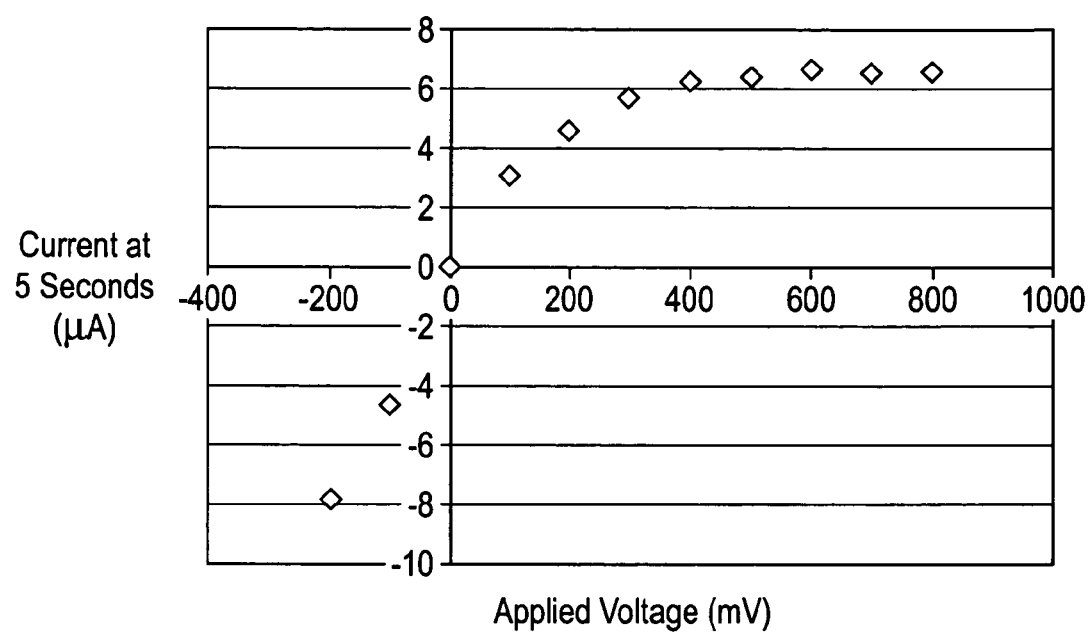
FIG. 3 is a hydrodynamic voltammogram illustrating the dependence of applied voltage with measured current.

FIG. 3 is a hydrodynamic voltammogram illustrating the dependence of applied voltage with measured current where ferri/ferrocyanide is the redox mediator and carbon is the working electrode. Each data point on the graph represents at least one experiment where a current is measured 5 seconds after applying a voltage across a working electrode and a reference electrode. FIG. 3 shows that the current forms an onset of a plateau region at about 400 mV because the applied voltage is sufficiently greater than of the E° value of ferrocyanide. Thus, as illustrated in FIG. 3, as the potential reaches approximately 400 mV, the glucose current becomes saturated because the oxidation of ferrocyanide is diffusion limited (i.e. the diffusion of ferrocyanide to the working electrode limits the magnitude of the measured current and is not limited by the electron transfer rate between ferrocyanide and the electrode).

In general, current generated by the oxidation of interfering compounds is not saturated by increases in applied voltage and shows a much stronger dependence on applied potential than current generated by oxidation of ferrocyanide (the ferrocyanide having been generated from the interaction of glucose with the enzyme and the enzyme with ferrocyanide. Typically, interfering compounds have slower electron transfer kinetics than redox mediators (i.e. ferrocyanide). This difference is ascribed to the fact that most interfering compounds undergo an inner sphere electron transfer pathway as opposed to the faster outer sphere electron transfer pathway of ferrocyanide. A typical inner sphere electron transfer requires a chemical reaction to occur, such as a hydride transfer, before transferring an electron. In contrast, an outer sphere electron transfer does not require a chemical reaction before transferring an electron. Therefore, inner sphere electron transfer rates are typically slower than outer sphere electron transfers because they require an additional chemical reaction step. The oxidation of ascorbate to dehydroascorbate is an example of an inner sphere oxidation that requires the liberation of two hydride moieties. The oxidation of ferrocyanide to ferricyanide is an example of an outer sphere electron transfer. Therefore, the current generated by interfering compounds generally increases when testing at a higher potential.

A relationship between an interfering compound current at the first working electrode and an interfering compound overpotential current at the second working electrode can be described by the following equation, $$Y \times I_1 = I_2 \qquad \text{(eq 2)}$$

where Y is an interfering compound dependent voltage effect factor, $I_1$ is the interfering compound current, and $I_2$ is the interfering compound overpotential current. Because the interfering compound voltage effect factor Y is dependent upon a number of factors, including, the particular interfering compound or compounds of concern and the material used for the working electrodes, calculation of a particular interfering compound dependent voltage effect factor for a particular system, test strip, analyte and interfering compound or compounds may require experimentation to optimize the voltage effect factor for those criteria. Alternatively, under certain circumstances, appropriate voltage effect factors may be derived or described mathematically.

In an embodiment of the present invention where ferri/ferrocyanide is the redox mediator and carbon is the working electrode, the interfering compound dependent voltage effect factor Y could be mathematically described using the Tafel equation for $I_1$ and $I_2$, $$I_1 = a' \exp\left(\frac{\eta_1}{b'}\right) \qquad \text{(eq 2a)}$$

$$I_2 = a' \exp\left(\frac{\eta_2}{b'}\right) \qquad \text{(eq 2b)}$$

where $\eta_1 = E_1 - E°$, $\eta_2 = E_2 - E°$, b' is a constant depending of the specific electroactive interfering compound, $E_1$ is the first potential, and $E_2$ is the second potential. The value of E° (the standard potential of a specific interfering compound) is not important because it is canceled out in the calculation of $\Delta\eta$. Equations 2, 2a, 2b can be combined and rearranged to yield the following equation, $$Y = \exp\left(\frac{\Delta\eta}{b'}\right) \qquad \text{(eq 2c)}$$

where $\Delta\eta = E_1 - E_2$. Equation 2c provides a mathematical relationship describing the relationship between $\Delta\eta$ (i.e. the difference between the first potential and the second potential) and the interfering compound dependent voltage effect factor Y. In an embodiment of the present invention, Y may range from about 1 to about 100, and more preferably between about 1 and 10. In an embodiment of this invention, the interfering compound dependent voltage effect factor Y may be determined experimentally for a specific interfering compound or combination of interfering compounds. It should be noted that the interfering compound dependent voltage effect factor Y for interfering compounds is usually greater than voltage effect factor $X_G$ for glucose. As the following sections will describe, the mathematical relationship of a) the interfering compound current $I_1$ and the interfering compound overpotential current $I_2$; and b) the glucose current $A_{1G}$ and the glucose overpotential current $A_{2G}$ will allow a glucose algorithm to be proposed which will reduce the effects of interfering compounds for measuring glucose.

In an embodiment of the present invention, an algorithm was developed to calculate a corrected glucose current (i.e. $A_{1G}$ and $A_{2G}$) which is independent of interferences. After dosing a sample onto a test strip, a first potential is applied to the first working electrode and a second potential is applied to the second working electrode. At the first working electrode, a first current is measured which can be described by the following equation, $$W_1 = A_{1G} + I_1 \qquad \text{(eq 3)}$$

where $W_1$ is the first current at the first working electrode. In other words, the first current includes a superposition of the glucose current $A_{1G}$ and the interfering compound current $I_1$. More specifically, the interfering compound current may be a direct interfering current which has been described hereinabove. At the second working electrode, a second current is measured at the second potential or overpotential which can be described by the following equation, $$W_2 = A_{2G} + I_2 \quad \text{(eq 4)}$$

where $W_2$ is the second current at the second working electrode, $A_{2G}$ is the glucose overpotential current measured at the second potential, and $I_2$ is the interfering compound overpotential current measured at the second potential. More specifically, the interfering compound overpotential current may be a Direct Interfering compound Current which has been described hereinabove. Using the previously described 4 equations (eq's 1 to 4) which contain 4 unknowns ($A_{1G}$, $A_{2G}$, $I_1$, and $I_2$), it is now possible to calculate a corrected glucose current equation which is independent of interfering compounds.

As the first step in the derivation, $A_{2G}$ from eq 1 and $I_2$ from eq 2 can be substituted into eq 4 to give the following eq 5.

$$W_2 = X_G A_{1G} + Y I_1 \quad \text{(eq 5)}$$

Next, eq 3 is multiplied by interfering compound dependent voltage effect factor Y for interfering compounds to give eq 6.

$$Y W_1 = Y A_{1G} + Y I_1 \quad \text{(eq 6)}$$

Eq 5 can now be subtracted from eq 6 to give the following form shown in eq 7

$$W_2 - Y W_1 = X_G A_{1G} - Y A_{1G} \quad \text{(eq 7)}$$

Eq 7 can now be rearranged to solve for the corrected glucose current $A_{1G}$ measured at the first potential as shown in eq 8.

$$A_{1G} = \frac{W_2 - Y W_1}{X_G - Y} \quad \text{(eq 8)}$$

Eq 8 outputs a corrected glucose current $A_{1G}$ which removes the effects of interferences requiring only the current output of the first working electrode and second working electrode (eg $W_1$ and $W_2$), glucose dependent voltage effect factors $X_G$, and interfering compound dependent voltage effect factor Y for interfering compounds.

A glucose meter containing electronics is electrically interfaced with a glucose test strip to measure the current from $W_1$ and $W_2$. In one embodiment of the present invention, $X_G$ and Y may be programmed into the glucose meter as read only memory. In another embodiment of the present invention, $X_G$ and Y may be transferred to the meter via a calibration code chip. The calibration code chip would have in its memory a particular set of values for $X_G$ and Y which would be calibrated for a particular lot of test strips. This would account for test strip lot-to-lot variations that may occur in $X_G$ and Y.

In another embodiment of the present invention, the corrected glucose current in eq 8 may be used by the meter only when a certain threshold is exceeded. For example, if $W_2$ is about 10% or greater than $W_1$, then the meter would use eq 8 to correct for the current output. However, if $W_2$ is about 10% or less than $W_1$, the interfering compound concentration is low and thus the meter can simply take an average current value between $W_1$ and $W_2$ to improve the accuracy and precision of the measurement. Instead of simply averaging the current of $W_1$ and $W_2$, a more accurate approach may be to average $W_1$ with $$\frac{W_2}{X_G}$$

where the glucose dependent voltage effect factor $X_G$ is taken into account (note $$\frac{W_2}{X_G}$$

approximately equals $A_{1G}$ according to eq 1 and 4 when $I_2$ is low). The strategy of using eq 8 only under certain situations where it is likely that a significant level of interferences are in the sample mitigates the risk of overcorrecting the measured glucose current. It should be noted that when $W_2$ is sufficiently greater than $W_1$ by a large amount (e.g. about 100% or more), this is an indicator of having an unusually high concentration of interferences. In such a case, it may be desirable to output an error message instead of a glucose value because a very high level of interfering compounds may cause a breakdown in the accuracy of eq 8.

The following sections will describe a possible test strip embodiment which may be used with the proposed algorithm of the present invention as shown in eq 8. FIG. 1 is an exploded perspective view of test strip 600, which includes six layers disposed upon a base substrate 5. These six layers are a conductive layer 50, an insulation layer 16, a reagent layer 22, an adhesive layer 60, a hydrophilic layer 70, and a top layer 80. Test strip 600 may be manufactured in a series of steps wherein the conductive layer 50, insulation layer 16, reagent layer 22, adhesive layer 60 are deposited on base substrate 5 using, for example, a screen printing process. Hydrophilic layer 70 and top layer 80 may be deposed from a roll stock and laminated onto base substrate 5. The fully assembled test strip forms a sample receiving chamber that can accept a blood sample so that it can be analyzed.

Conductive layer 50 includes reference electrode 10, first working electrode 12, second working electrode 14, a first contact 13, a second contact 15, a reference contact 11, and a strip detection bar 17. Suitable materials which may be used for the conductive layer are Au, Pd, Ir, Pt, Rh, stainless steel, doped tin oxide, carbon, and the like. Preferably, the material for the conductive layer may be a carbon ink such as those described in U.S. Pat. No. 5,653,918.

Insulation layer 16 includes cutout 18 which exposes a portion of reference electrode 10, first working electrode 12, and second working electrode 14 which can be wetted by a liquid sample. As a non-limiting example, insulation layer (16 or 160) may be Ercon E6110-116 Jet Black Insulayer Ink which may be purchased from Ercon, Inc.

Reagent layer 22 may be disposed on a portion of conductive layer 50 and insulation layer 16. In an embodiment of the present invention, reagent layer 22 may include chemicals such as a redox enzyme and redox mediator which selectivity react with glucose. During this reaction, a proportional amount of a reduced redox mediator can be generated that then can be measured electrochemically so that a glucose concentration can be calculated. Examples of reagent formulations or inks suitable for use in the present invention can be found in U.S. Pat. Nos. 5,708,247 and 6,046,051; published international applications WO01/67099 and WO01/73124, all of which are incorporated by reference herein.

Adhesive layer 60 includes first adhesive pad 24, second adhesive pad 26, and third adhesive pad 28. The side edges of first adhesive pad 24 and second adhesive pad 26 located adjacent to reagent layer 22 each define a wall of a sample receiving chamber. In an embodiment of the present invention, the adhesive layer may comprise a water based acrylic copolymer pressure sensitive adhesive which is commercially available from Tape Specialties LTD in Tring, Herts, United Kingdom (part#A6435).

Hydrophilic layer 70 includes a distal hydrophilic pad 32 and proximal hydrophilic pad 34. As a non-limiting example, hydrophilic layer 70 be a polyester having one hydrophilic surface such as an anti-fog coating which is commercially available from 3M. It should be noted that both distal hydrophilic film 32 and proximal hydrophilic film 34 are visibly transparent enabling a user to observe a liquid sample filling the sample receiving chamber.

Top layer 80 includes a clear portion 36 and opaque portion 38. Top layer 80 is disposed on and adhered to hydrophilic layer 70. As a non-limiting example, top layer 40 may be a polyester. It should be noted that the clear portion 36 substantially overlaps proximal hydrophilic pad 32 which allows a user to visually confirm that the sample receiving chamber is sufficiently filled. Opaque portion 38 helps the user observe a high degree of contrast between a colored fluid such as, for example, blood within the sample receiving chamber and the opaque section of the top film.

Figure 2:
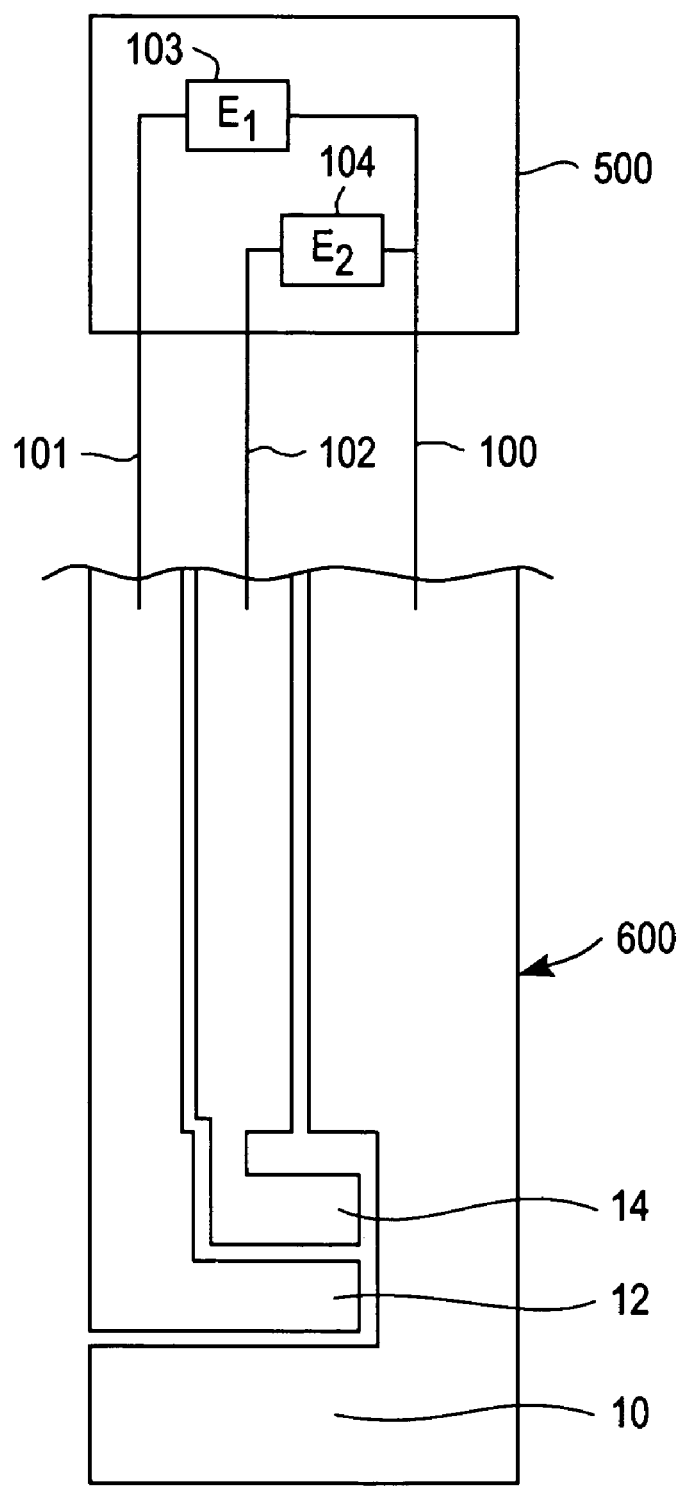
FIG. 2 is a schematic view of a meter and strip for use in the present invention.

FIG. 2 is a simplified schematic showing a meter 500 interfacing with a test strip 600. Meter 500 has three electrical contacts that form an electrical connection to first working electrode 12, second working electrode 14, and reference electrode 10. In particular connector 101 connects voltage source 103 to first working electrode 12, connector 102 connects voltage source 104 to second working electrode 14 and common connector 100 connects voltage source 103 and 104 to reference electrode 10. When performing a test, voltage source 103 in meter 500 applies a first potential $E_1$ between first working electrode 12 and reference electrode 10 and voltage source 104 applies a second potential $E_2$ between second working electrode 14 and reference electrode 10. A sample of blood is applied such that first working electrode 12, second working electrode 14, and reference electrode 10 are covered with blood. This causes reagent layer 22 to become hydrated which generates ferrocyanide in an amount proportional to the glucose and/or interfering compound concentration present in the sample. After about 5 seconds from the sample application, meter 500 measures an oxidation current for both first working electrode 12 and second working electrode 14.

In the previously described first and second test strip embodiments, the first working electrode 12 and second working electrode 14 had the same area. It should be noted that the present invention is not limited to test strips having equal areas. For alternative embodiments to the previously described strips where the areas are different, the current output for each working electrode must be normalized for area. Because the current output is directly proportional to area, the terms within Equation 1 to Equation 8 may be in units of amperes (current) or in amperes per unit area (i.e. current density).

It will be recognized that equivalent structures may be substituted for the structures illustrated and described herein and that the described embodiment of the invention is not the only structure that may be employed to implement the claimed invention. In addition, it should be understood that every structure described above has a function and such structure can be referred to as a means for performing that function. While preferred embodiments of the present invention have been shown and described herein, it will be obvious to those skilled in the art that such embodiments are provided by way of example only. Numerous variations, changes, and substitutions will now occur to hose skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of reducing interferences in an electrochemical sensor having a sample chamber with first and second working electrodes disposed in the chamber, the working electrodes including a reagent disposed thereon, the method comprising:

contacting a sample of physiological fluid with the working electrodes and reagent, the physiological fluid including at least an analyte disposed therein;

applying a first potential to the first working electrode to initiate a chemical reaction;

applying a second potential to the second working electrode to initiate a chemical reaction, wherein said second potential is greater than the absolute value of said first potential;

measuring a first current, at said first working electrode, which comprises an analyte current and an interfering compound current;

measuring a second current, at said second working electrode, which comprises an analyte overpotential current and an interfering compound overpotential current, wherein said analyte overpotential current has a first directly proportional relationship to said analyte current, the first directly proportional relationship comprising $$X \times A_1 = A_2$$

where X is said analyte voltage effect factor derived from calibration test data of the sensor, $A_1$ is said analyte current, and $A_2$ is said analyte overpotential current and, wherein said interfering compound overpotential current has a second directly proportional relationship to said interfering compound current, the second directly proportional relationship is $$Y \times I_1 = I_2$$

where Y is said interfering compound voltage effect factor, $I_1$ is said interfering compound current, and $I_2$ is said interfering compound over potential current; and calculating a corrected current value representative of an analyte concentration of the physiological fluid using an equation which is a function of said first current, said second current, said first directly proportional relationship, and said second directly proportional relationship.

2. The method of claim 1, wherein said equation is $$A_1 = \frac{W_2 - YW_1}{X - Y}$$

where $A_1$ is said analyte current, $W_1$ is said first current, $W_2$ is said second current, X is an analyte voltage effect factor, and Y is an interfering compound voltage effect factor.

3. The method of claim 1, wherein said analyte is glucose.

4. The method of claim 1, wherein said first potential is between about 385 millivolts and about 415 millivolts for said electrochemical sensor which comprises a carbon working electrode and a ferrocyanide redox mediator.

5. The method of claim 1, wherein said second potential is between about 420 millivolts and about 1000 millivolts for said electrochemical sensor which comprises a carbon working electrode and a ferrocyanide redox mediator.

6. The method of claim 1, wherein said interfering compound current results from the oxidation of at least one chemical chosen from the group consisting of acetaminophen, ascorbic acid, bilirubin, dopamine, gentisic acid, glutathione, levodopa, methyldopa, tolazimide, tolbutamide, and uric acid.

* * * * *